(12) United States Patent
Gatzemeyer et al.

(10) Patent No.: US 7,900,309 B2
(45) Date of Patent: Mar. 8, 2011

(54) POWERED TOOTHBRUSH

(75) Inventors: John J. Gatzemeyer, Hillsborough, NJ (US); Eduardo Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/198,474

(22) Filed: Aug. 26, 2008

(65) Prior Publication Data

US 2008/0313830 A1 Dec. 25, 2008

Related U.S. Application Data

(60) Division of application No. 11/130,273, filed on May 17, 2005, now Pat. No. 7,430,778, which is a division of application No. 10/260,583, filed on Sep. 27, 2002, now Pat. No. 6,892,412, which is a continuation-in-part of application No. 10/066,459, filed on Jan. 31, 2002, now abandoned.

(51) Int. Cl.
A61C 17/34 (2006.01)
(52) U.S. Cl. .................. 15/22.2; 15/22.1; 15/28
(58) Field of Classification Search ............ 15/22.1, 15/22.2, 28
See application file for complete search history.

(56) References Cited

U.S. PATENT DOCUMENTS

| | | | |
|---|---|---|---|
| 1,255,028 A | 1/1918 | Leonard et al. | |
| 1,796,641 A | 3/1931 | Zimmerman et al. | |
| 2,140,307 A | 12/1938 | Belaschk et al. | |
| 2,215,031 A | 9/1940 | Elmore | |
| 2,379,049 A | 6/1945 | Tompkins | |
| 3,103,027 A | 9/1963 | Birch | |
| 3,129,449 A | 4/1964 | Cyzer | |
| 3,230,562 A | 1/1966 | Birch | |
| 3,242,516 A | 3/1966 | Cantor | |
| 3,577,579 A | 5/1971 | Duve et al. | |
| 4,081,876 A | 4/1978 | Pugh | |
| 4,156,620 A | 5/1979 | Clemens | |
| 4,274,173 A | 6/1981 | Cohen | |
| 4,479,516 A | 10/1984 | Hunter | |
| 4,766,630 A | 8/1988 | Hegemann | |
| 4,795,347 A | 1/1989 | Maurer | |
| 4,827,550 A | 5/1989 | Graham et al. | |
| 4,845,795 A | 7/1989 | Crawford et al. | |
| 4,894,880 A | 1/1990 | Aznavoorian | |
| 4,989,287 A | 2/1991 | Scherer | |
| 5,046,213 A | 9/1991 | Curtis et al. | |
| 5,068,939 A | 12/1991 | Holland | |
| 5,070,567 A | 12/1991 | Holland | |

(Continued)

FOREIGN PATENT DOCUMENTS

CA 1082408 7/1980

(Continued)

*Primary Examiner* — Randall Chin
(74) *Attorney, Agent, or Firm* — Judy Chung

(57) ABSTRACT

The head of a powered toothbrush includes a first tuft block mounted for rotational oscillation about an axis generally perpendicular to the outer surface of the head, and a second tuft block having fixed bristles or bristles independently movable by being mounted on an elastomeric base. The second tuft block oscillates perpendicular to a longitudinal axis of the head and in an in and out direction perpendicular to the outer surface of the head. A third stationary block may also be mounted on the head of the powered toothbrush. The bristles on the first, second, and third tuft blocks may be of various lengths, colors and stiffness, and may be mounted perpendicularly to or at an angle to the outer surface of the head.

9 Claims, 3 Drawing Sheets

U.S. PATENT DOCUMENTS

| | | |
|---|---|---|
| 5,077,855 A | 1/1992 | Ambasz |
| 5,088,145 A | 2/1992 | Whitefield |
| 5,099,536 A | 3/1992 | Hirabayashi |
| D330,286 S | 10/1992 | Curtis et al. |
| 5,170,525 A | 12/1992 | Cafaro |
| 5,177,826 A | 1/1993 | Vrignaud et al. |
| D334,473 S | 4/1993 | Volpenhein et al. |
| 5,226,206 A | 7/1993 | Davidovitz et al. |
| 5,259,083 A | 11/1993 | Stansbury, Jr. |
| 5,335,389 A | 8/1994 | Curtis et al. |
| 5,353,460 A | 10/1994 | Bauman |
| 5,359,747 A | 11/1994 | Amakasu |
| 5,390,984 A | 2/1995 | Boucherie et al. |
| 5,392,483 A | 2/1995 | Heinzelman et al. |
| 5,404,608 A | 4/1995 | Hommann |
| 5,416,942 A | 5/1995 | Baldacci et al. |
| 5,435,034 A | 7/1995 | Bigler et al. |
| 5,446,940 A | 9/1995 | Curtis et al. |
| 5,500,970 A | 3/1996 | Maurer et al. |
| 5,504,958 A | 4/1996 | Herzog |
| 5,504,959 A | 4/1996 | Yukawa et al. |
| 5,504,960 A | 4/1996 | Hommann |
| 5,524,312 A | 6/1996 | Tan et al. |
| 5,528,786 A * | 6/1996 | Porat et al. .................. 15/22.1 |
| 5,533,791 A | 7/1996 | Boucherie |
| 5,609,890 A | 3/1997 | Boucherie |
| 5,617,601 A | 4/1997 | McDougall |
| 5,617,603 A | 4/1997 | Mei |
| 5,625,916 A | 5/1997 | McDougall |
| 5,727,273 A | 3/1998 | Pai |
| 5,732,432 A | 3/1998 | Hui |
| 5,732,433 A | 3/1998 | Gocking et al. |
| 5,735,011 A | 4/1998 | Asher |
| 5,764,743 A | 6/1998 | Goedken et al. |
| 5,784,743 A | 7/1998 | Shek |
| 5,799,354 A | 9/1998 | Amir |
| 5,822,821 A | 10/1998 | Sham |
| RE35,941 E | 11/1998 | Stansbury, Jr. |
| 5,836,030 A | 11/1998 | Hazeu et al. |
| 5,850,655 A | 12/1998 | Gocking et al. |
| 5,876,206 A | 3/1999 | Maurer |
| 5,974,613 A | 11/1999 | Herzog |
| 6,000,083 A | 12/1999 | Blaustein et al. |
| 6,006,394 A | 12/1999 | Bredall et al. |
| 6,021,538 A * | 2/2000 | Kressner et al. ................... 15/28 |
| 6,032,313 A | 3/2000 | Tsang |
| 6,138,310 A | 10/2000 | Porper et al. |
| D434,563 S | 12/2000 | Lim et al. |
| 6,178,579 B1 | 1/2001 | Blaustein et al. |
| 6,189,693 B1 | 2/2001 | Blaustein et al. |
| 6,237,178 B1 | 5/2001 | Krammer et al. |
| 6,308,358 B2 | 10/2001 | Gurber et al. |
| 6,314,606 B1 | 11/2001 | Hohlbein |
| 6,360,395 B2 | 3/2002 | Blaustein et al. |
| 6,371,294 B1 | 4/2002 | Blaustein et al. |
| 6,434,773 B1 | 8/2002 | Kuo |
| 6,453,498 B1 | 9/2002 | Wu |
| 6,463,615 B1 | 10/2002 | Gruber et al. |
| 6,510,575 B2 | 1/2003 | Calabrese |
| 6,553,604 B1 | 4/2003 | Braun |
| 6,564,416 B1 | 5/2003 | Claire et al. |
| 6,574,820 B1 | 6/2003 | DePuydt et al. |
| 6,725,490 B2 * | 4/2004 | Blaustein et al. .............. 15/22.2 |
| 7,552,497 B2 | 6/2009 | Gatzemeyer |
| 2001/0001334 A1 | 5/2001 | Gruber et al. |
| 2001/0004781 A1 | 6/2001 | Blaustein et al. |
| 2001/0022277 A1 | 9/2001 | Blaustein et al. |
| 2002/0032941 A1 | 3/2002 | Blaustein et al. |
| 2002/0162180 A1 | 11/2002 | Blaustein et al. |
| 2003/0066145 A1 | 4/2003 | Prineppi |
| 2003/0084525 A1 | 5/2003 | Blaustein et al. |
| 2003/0084526 A1 | 5/2003 | Brown et al. |
| 2003/0084528 A1 | 5/2003 | Chan et al. |
| 2003/0140435 A1 | 7/2003 | Eliav et al. |
| 2003/0140436 A1 | 7/2003 | Gatzemeyer et al. |
| 2003/0140437 A1 | 7/2003 | Eliav et al. |
| 2003/0182743 A1 | 10/2003 | Gatzemeyer et al. |
| 2003/0182744 A1 | 10/2003 | Fattori et al. |
| 2003/0182746 A1 | 10/2003 | Fattori et al. |
| 2003/0221270 A1 | 12/2003 | Kuo |
| 2004/0010869 A1 | 1/2004 | Fattori et al. |
| 2004/0045105 A1 | 3/2004 | Eliav et al. |
| 2004/0049867 A1 | 3/2004 | Hui |
| 2004/0060133 A1 | 4/2004 | Eliav |
| 2004/0060134 A1 | 4/2004 | Eliav et al. |
| 2004/0060135 A1 | 4/2004 | Gatzemeyer et al. |
| 2004/0060137 A1 | 4/2004 | Eliav |
| 2004/0083566 A1 | 5/2004 | Blaustein et al. |
| 2004/0084063 A1 | 5/2004 | Vago et al. |
| 2004/0123409 A1 | 7/2004 | Dickie |
| 2004/0143917 A1 | 7/2004 | Ek |
| 2004/0168272 A1 | 9/2004 | Prineppi |
| 2004/0177458 A1 | 9/2004 | Chan et al. |
| 2004/0177462 A1 | 9/2004 | Brown, Jr. et al. |

FOREIGN PATENT DOCUMENTS

| | | |
|---|---|---|
| CA | 2141569 | 1/2000 |
| CA | 2462435 | 5/2003 |
| CN | 2236827 Y | 10/1996 |
| CN | 2271352 Y | 12/1997 |
| CN | 2271353 Y | 12/1997 |
| CN | 2324988 Y | 6/1999 |
| CN | 1644183 | 7/2005 |
| DE | 27 36 286 | 12/1978 |
| DE | 84 26 426.8 | 3/1985 |
| DE | 3406112 A1 | 8/1985 |
| DE | 44 12 301 A1 | 10/1995 |
| DE | 296 00 236 U1 | 4/1996 |
| DE | 296 13 608 U1 | 11/1996 |
| DE | 296 18 755 U1 | 3/1997 |
| DE | 298 09 977 U1 | 2/1999 |
| DE | 29 82 112 1 U | 3/1999 |
| DE | 103 15 011 A1 | 5/2004 |
| EP | 0 208 401 B1 | 5/1991 |
| EP | 0 254 397 B1 | 7/1991 |
| EP | 0 460 610 A | 12/1991 |
| EP | 0 488 971 A2 | 6/1992 |
| EP | 0 546 203 B1 | 8/1996 |
| EP | 0 520 985 B1 | 8/1997 |
| EP | 1 053 721 A1 | 11/2000 |
| EP | 1 059 049 A1 | 12/2000 |
| EP | 1 093 770 A2 | 4/2001 |
| EP | 1 139 908 A1 | 5/2001 |
| EP | 1 132 057 A1 | 9/2001 |
| EP | 1 385 448 | 11/2002 |
| EP | 1 386 589 A1 | 2/2004 |
| EP | 1 093 770 B1 | 3/2004 |
| EP | 1 402 846 A2 | 3/2004 |
| FR | 1250455 | 12/1960 |
| FR | 2548528 | 1/1985 |
| GB | 452961 | 9/1936 |
| GB | 1583558 | 1/1981 |
| GB | 2228861 A | 9/1990 |
| GB | 2237505 A | 5/1991 |
| GB | 2 247 297 * | 2/1992 |
| GB | 2290224 A | 12/1995 |
| GB | 2319170 A | 5/1998 |
| JP | 3001895 | 6/1905 |
| JP | 57-89810 | 6/1982 |
| JP | 61-131706 | 6/1986 |
| JP | 62-49806 | 3/1987 |
| JP | 63-183822 | 11/1988 |
| JP | 1-066704 | 3/1989 |
| JP | 1-141631 | 9/1989 |
| JP | 2-22121 | 2/1990 |
| JP | 2-218309 | 8/1990 |
| JP | 4-77326 | 7/1992 |
| JP | 4-133733 | 12/1992 |
| JP | 5-146314 | 6/1993 |
| JP | 5-161509 | 6/1993 |
| JP | 5-199918 | 8/1993 |
| JP | 5-269024 | 10/1993 |
| JP | 5-93253 | 12/1993 |
| JP | 6-189822 | 7/1994 |
| JP | 6-506617 | 7/1994 |
| JP | 7-116023 | 5/1995 |
| JP | 7-116024 | 5/1995 |

| | | | | | | |
|---|---|---|---|---|---|---|
| JP | 2511226 | 7/1996 | | WO | WO 96/37164 | 11/1996 |
| JP | 9-168496 | 6/1997 | | WO | WO 97/24079 | 7/1997 |
| JP | 2811246 | 8/1998 | | WO | WO 98/23223 | 6/1998 |
| JP | 11-501247 | 2/1999 | | WO | WO 99/23910 | 5/1999 |
| JP | 3063406 | 8/1999 | | WO | WO 00/39379 | 7/2000 |
| JP | 11-342140 | 12/1999 | | WO | WO 00/74592 A1 | 12/2000 |
| JP | 2000-505690 | 5/2000 | | WO | WO 00/78244 A1 | 12/2000 |
| JP | 2000-507489 | 6/2000 | | WO | WO0076369 | 12/2000 |
| KR | 91-700015 | 3/1991 | | WO | WO 01/21094 A1 | 3/2001 |
| RU | 2039508 | 7/1995 | | WO | WO 01/32095 A1 | 5/2001 |
| RU | 2130748 | 5/1999 | | WO | WO0143586 | 6/2001 |
| TW | 135303 | 5/1905 | | WO | WO 01/89344 A1 | 11/2001 |
| TW | 257968 | 6/1905 | | WO | WO 01/91603 A1 | 12/2001 |
| TW | 154730 | 3/1979 | | WO | WO 02/087464 A1 | 11/2002 |
| TW | 164493 | 7/1979 | | WO | WO 03/020159 A1 | 3/2003 |
| TW | 200663 | 5/1981 | | WO | WO 03/039393 A1 | 5/2003 |
| TW | 274724 | 4/1984 | | WO | WO 03/039394 A1 | 5/2003 |
| TW | 311444 | 12/1985 | | WO | WO 03/039395 A2 | 5/2003 |
| TW | 212909 | 9/1993 | | WO | WO 03/039396 A1 | 5/2003 |
| TW | 239963 | 2/1995 | | WO | WO 03/039397 A1 | 5/2003 |
| TW | 253174 | 8/1995 | | WO | WO 03/063723 A1 | 8/2003 |
| TW | 334345 | 6/1998 | | WO | WO 03/077790 A1 | 9/2003 |
| TW | 406557 | 9/2000 | | WO | WO03082049 | 10/2003 |
| WO | WO 90/09123 | 8/1990 | | WO | WO 2004/028294 A1 | 4/2004 |
| WO | WO 95/11636 | 5/1995 | | | | |

\* cited by examiner

POWERED TOOTHBRUSH

CROSS REFERENCE TO RELATED APPLICATIONS

The present application is a continuation-in-part application of Ser. No. 10/066,459, filed Jan. 31, 2002, the disclosure of which is incorporated by reference herein in its entirety.

BACKGROUND OF THE INVENTION

1. Field of the Invention

The present invention relates generally to toothbrushes, and, more particularly, to a powered toothbrush having a head with a plurality of movably mounted bristle sections.

2. Description of the Related Art

Various types of powered toothbrushes are generally known in the art. For example, U.S. Pat. No. 5,625,916 discloses an electrically driven toothbrush having a motor drive for rotating a drive shaft. The drive shaft connects to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

U.S. Pat. No. 5,416,942 shows a further type of powered toothbrush wherein the head includes a pair of concentrically arranged sections, each of which is driven in a rotationally oscillating manner in opposite directions. The toothbrush head includes the two counter-oscillating sections, but does not include any other sections onto which bristles may be mounted.

U.S. Pat. No. 6,032,313 discloses a household appliance such as a toothbrush that may be used for cleaning, polishing, or massaging. The head of the appliance includes a plurality of co-axially rotatable or parallel linearly-movable sections, but fails to provide other bristle-containing sections.

U.S. Pat. No. 5,070,567 discloses an electrically-driven toothbrush that includes a rotatable brush head having bristles thereon. A further group of bristles, each of which rotates around its own axis, reside adjacent to the brush head. U.S. Pat. No. 1,796,641 relates to a spotting brush for dry-cleaning that includes a pair of rotatably mounted side-by-side heads.

None of the powered toothbrushes of the related art includes two separate, movable bristle sections or tuft blocks. Thus, there is a need in the art for a powered toothbrush having more than one movable bristle section or tuft block to enhance the cleaning efficiency of the toothbrush.

OBJECTS OF THE INVENTION

It is a general object of the present invention to provide a powered toothbrush which avoids the aforementioned deficiencies of the known prior art.

It is also an object of the present invention to provide a powered toothbrush which enhances the cleaning efficiency of the toothbrush head.

It is a further object of the present invention to provide a powered toothbrush which includes two separate, movable bristle sections or tuft blocks.

It is yet another object of the present invention to provide a powered toothbrush which includes a rotationally oscillating section and a linearly oscillating section both of which have bristles for delivery of a cleaning, polishing, and whitening action.

It is still a further object of the present invention to provide a powered toothbrush which is similar in appearance to a manual toothbrush.

Various other objects, advantages and features of the present invention will become readily apparent from the ensuing detailed description and the novel features will be particularly pointed out in the appended claims.

SUMMARY OF THE INVENTION

The present invention solves the problems of the related art by providing a powered toothbrush which includes a rotationally oscillating section, a linearly oscillating section, and, optionally, a stationary section, all of which have bristles for delivery of a cleaning, polishing, whitening action in addition to enhancing the cleaning efficiency of a typical powered toothbrush.

As embodied and described herein, the present invention is broadly drawn to a powered toothbrush having a handle with a neck, and a head removably connected to the neck and having an exposed outer surface. A first tuft block is mounted to the head and includes a first array of bristles extending outwardly from the exposed outer surface of the head. A first drive member is operatively connected to the first tuft block for moving the first tuft block about an axis generally perpendicular to the exposed outer surface. A second tuft block is mounted to the head and includes a second array of bristles extending outwardly from the exposed outer surface of the head. A second drive member is operatively connected to the second tuft block for moving the second tuft block in a direction generally perpendicular to the exposed outer surface of the head.

In various embodiments of the present invention, the second tuft block oscillates back and forth in a direction perpendicular to the longitudinal axis of the toothbrush head or in a direction parallel to the longitudinal axis of the toothbrush head. In yet an alternative embodiment of the present invention, the second tuft block is capable of oscillating in and out in a direction perpendicular to the outer surface of the toothbrush head to form a vibrating section.

In still another aspect of the present invention, a third stationary tuft block having a third array of bristles may be provided below the second tuft block towards the handle of the toothbrush. The second and third tuft blocks are preferably mounted longitudinally in alignment with the first tuft block so that the portion of the head containing the first, second and third array of bristles of respectively the first, second, and third tuft blocks is of an elongated shape which facilitates holding toothpaste on the bristles, and appear visually to be shaped like a conventional manual toothbrush.

Further scope of applicability of the present invention will become apparent from the detailed description given hereinafter. However, it should be understood that the detailed description and specific examples, while indicating preferred embodiments of the invention, are given by way of illustration only, and various changes and modifications within the spirit and scope of the invention will become readily apparent to those skilled in the art from this detailed description. It, is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF CERTAIN PREFERRED EMBODIMENTS OF THE PRESENT INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

FIGS. 1-6 illustrate a preferred embodiment of the present invention wherein a powered toothbrush 10 includes a neck section 12 of a handle 30, and a head 14 at one end of the neck section 12. Head 14 may be a refill head and thus be removably connected to the neck section 12, or head 14 may be permanently connected to the neck section 12 and still be in accordance with the teachings of the present invention.

Figure 1:
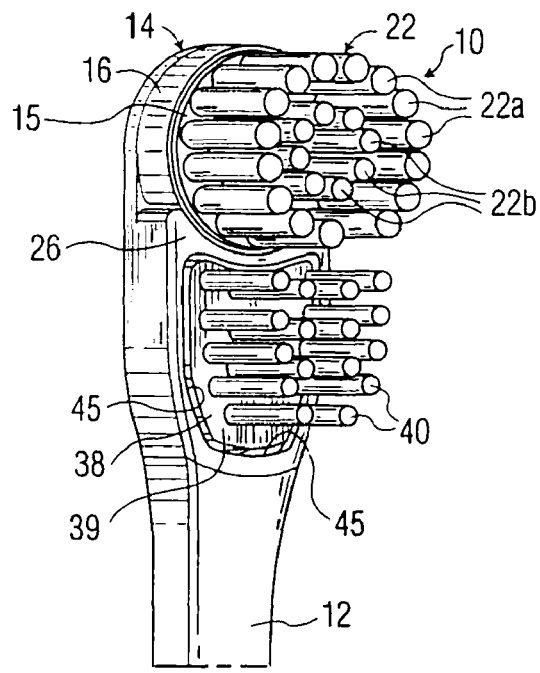
FIG. 1 is a perspective view of a preferred embodiment of a powered toothbrush head in accordance with the teachings of the present invention.
Figure 2:
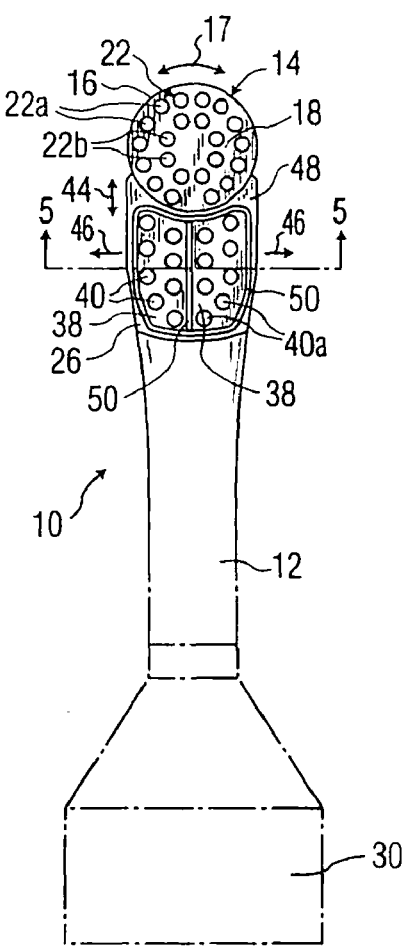
FIG. 2 is a front elevational view of the powered toothbrush head shown in FIG. 1.
Figure 3:
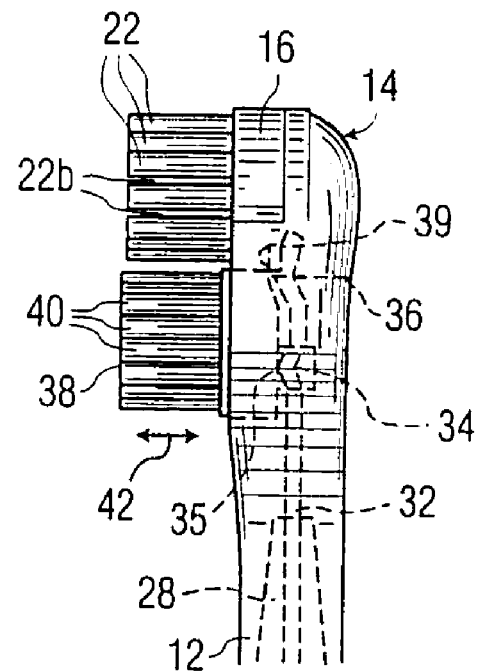
FIG. 3 is a side elevational view of a section of the powered toothbrush head shown in FIGS. 1-2.

As illustrated, particularly in FIGS. 1-3, head 14 includes a first tuft block 16 which is illustrated as being at the outermost or distal portion of head 14. First tuft block 16 is preferably in the general form of having a disk of circular ring-type shape, and oscillates in a rotational manner as indicated by arrow 17 in FIG. 2. Although a circular ring-type shape for the first tuft block 16 has been shown in FIGS. 1-2, other shapes, such as oval or various regular or irregular shapes, could be envisioned and still be in accordance with the teachings of the present invention. In one preferred embodiment of the invention, first tuft block 16 includes an inner area 18 which may include further bristles, or may include a second inner counter-oscillating tuft block, as disclosed in application Ser. No. 10/107,092, filed Mar. 26, 2002, now U.S. Pat. No. 7,552, 497, assigned to the assignee of the present application, Colgate-Palmolive Co., the disclosure of which being incorporated by reference herein in its entirety. A circular shape for first tuft block 16 is preferred since it requires the least amount of clearance to accommodate the oscillating motion and to potentially accommodate an inner counter-oscillating tuft block.

A first array of bristles 22 extends outwardly from the first tuft block 16. This first array of bristles 22 includes a first plurality of tufts or bristles 22a, arranged, in the illustrated embodiment, in a substantially circular arrangement. Similarly, the first array of bristles 22 includes a second plurality of tufts of bristles 22b provided in an inner area 18 of the first tuft block 16 which are also in a generally circular arrangement with each other along a generally circular path concentric with a first plurality of tufts or bristles 22a.

Figure 4:
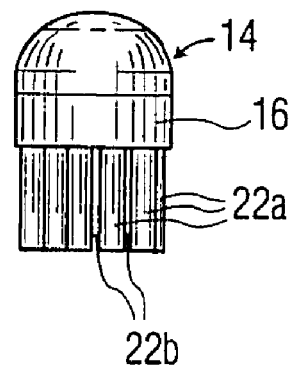
FIG. 4 is a top plan view of the powered toothbrush head shown in FIGS. 1-3.

The arrangement of the two concentric sets of bristles is preferred since such arrangement maximizes use of the surface area of first tuft block 16. In one preferred embodiment of the present invention, the outer circular arrangement of bristles 22a extend outwardly from the outer surface 26 of head 14 by a greater distance than the inner circular arrangement of bristles 22b, as best shown in FIGS. 3 and 4. As a result, a cup-like structure is formed which facilitates retaining toothpaste on the bristles 22a, 22b.

A characteristic of the toothbrush head of the present invention is the inclusion of a movable second tuft block 38 which is illustrated in FIG. 2 as being between neck 12 and first tuft block 16. It is to be understood, however, that second tuft block 38 could be located distally from, or laterally side-by-side to first tuft block 16. It is preferred, however, that second tuft block 38 be positioned toward the neck 12 of the toothbrush head (longitudinally outside of tuft block 16) so as to create a toothbrush head having a greater surface area.

The provision of second tuft block 38 is also advantageous in that powered toothbrush 10 simulates, in the appearance of head 14, the structure of a manual toothbrush. As a result, the powered toothbrush 10 of the present invention is more acceptable to users since the appearance is more familiar to the user. In addition, the pair of tuft blocks 16, 38 enhances the efficiency of toothbrush 10, both as a result of the movement of tuft blocks 16, 38, and of the ability to readily retain toothpaste thereon.

As illustrated, second tuft block 38 is provided in an opening 45 formed in a body portion 48 of head 14, wherein opening 45 is slightly larger than second tuft block 38 to accommodate movement of second tuft block 38 therein, such as oscillating movement of the second tuft block 38. Second tuft block 38 also includes a second array of bristles 40 which extend outwardly from an outer surface 39 thereof. Outer surface 39 of second tuft block 38, outer surface 26 of the body 48 of the head, and an outer surface 15 of first tuft block 16 are preferably coplanar with each other so that the outer surface of the entire head 14 is in a single contiguous plane. The invention, however, could be practiced where some or all of the tuft blocks extend outwardly by a different distance or by a difference angle than other tuft blocks to result in a stepped effect for the outer surface of the head 14.

In the illustrated embodiment as best shown in FIG. 3, the second array of bristles 40 extends outwardly from outer surface 26 of head 14 by approximately the same distance as the first array of bristles 22 so as to create a generally flat surface for receiving the toothpaste. Alternatively, however, some bristles may be shorter or at a different angle than the other bristles.

Figure 7:
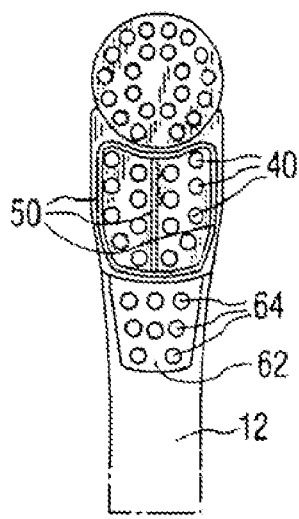
FIG. 7 is a front elevational view of another preferred embodiment of a powered toothbrush head in accordance with the teachings of the present invention.

In another preferred embodiment of the present invention, a third tuft block 62 may be fixedly attached to head 14 at a location above neck 12, but below second tuft block 38 (see FIG. 7). Third tuft block 62 includes a third array of bristles 64 extending outwardly therefrom by a distance equal to or different than the distance bristles 22, 40 extend outwardly from outer surface 26 of head 14. It is to be understood, however, that third tuft block 62 could be located distally from, or laterally side-by-side to first tuft block 16 or second tuft block 38. It is preferred, however, that third tuft block 62 be positioned closer to the neck section than the second tuft block 38 (longitudinally outside of second tuft block 38) so as to expand the surface area of the head 14 having bristles.

The provision of third tuft block 62 is also advantageous in that the head 14 of the powered toothbrush 10 simulates the structure of a manual toothbrush. As a result, the powered toothbrush 10 so formed is more acceptable to users since the appearance is more familiar. In addition, by employing three tuft blocks 16, 38, 62, the efficiency of toothbrush 10 is even further enhanced, both as a result of the movement of tuft blocks 16, 38, 62, and of the ability to readily retain toothpaste.

While FIGS. 1-7 illustrate conventional fiber form bristles, the term "bristles" as used herein is intended to be used in a generic sense as cleaning elements or massage elements and could include, for example, elastomeric fingers or walls arranged in a circular cross-section shape or any type of desired shape, including straight portions or sinusoidal portions.

The bristles could be mounted to the tuft blocks or sections by extending through suitable openings in the tuft blocks so that the base of the bristles is mounted within or below the tuft blocks. If desired, the bristles could be embedded in an elastomeric material which would permit the bristles to have an independent motion in addition to the motion imparted by the oscillating tuft blocks 16, 38, instead of being fixed bristles. Such various forms of bristles may thus be used for the bristles used in any section of head 14.

It is to be understood that the specific illustration of the bristles is merely for exemplary purposes. The invention can, however, be practiced with various combinations of the same or different bristle configurations (such as stapled, in-mold tufting (IMT) technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while FIGS. 1-7 illustrate the bristles to be generally perpendicular to the outer surface of head 14, some or all of the bristles may be angled at various angles with respect to the outer surface of the bristle head. It is thereby possible to select the combination of bristle configurations, bristle materials and bristle orientations to achieve specific intended results, such as to create as much movement from the oscillating tuft heads to deliver additional oral health benefits like enhanced cleaning, tooth polishing, tooth whitening and/or massaging of the gums.

It is to be understood that the invention can be practiced by locating tufts of bristles in any otherwise open area of the toothbrush head. Such tufts of bristles could be fixed bristles perpendicularly mounted or mounted at an angle to the exposed outer surface 26 of the head 14 or could be bristles mounted on an elastomeric base so as to be independently movable when pressure is applied. Such bristles in their normal condition could be either perpendicular or at an angle to the exposed outer surface of the toothbrush head.

The invention may also be practiced where different sets of bristles have different colors. Thus, for example, the arcuate row of bristles 22a could have a white color while the inner generally circular pattern of bristles 22b of the first array of bristles 22 could have a blue color. The arcuate row of bristles 40 at the portion of second tuft block 38 adjacent to neck 12 and the tuft of bristles within that arcuate row could also be of a blue color, while an inner patterned row of bristles 40 in the middle portion of second tuft block 38 could be of a white color. The final bristles 40 adjacent to the rotationally oscillating bristles 22, 24 could be of a green color. It is to be understood that the above description of specific color combinations is simply for exemplary purposes and any combination of colors including only one color could be used.

Tuft blocks 16 and 38 may be oscillated by any suitable drive mechanism. FIG. 3, for example, illustrates the type of drive mechanism described in U.S. Pat. No. 5,625,916, the disclosure of which being incorporated by reference herein in its entirety except where inconsistent with the express teachings of the present invention. As shown in FIG. 3, a drive shaft 28 is rotated by a driving motor (not shown) in the handle 30. The driving motor may be powered in any suitable manner such as with batteries. A transmission spindle 32 is operatively connected, such as by a permanent or detachable connection, to drive shaft 28. Transmission spindle 32 has two projections oriented eccentrically with respect to the axis of rotation of drive shaft 28. A first projection 36 acts as a cam surface and engages an axial slot 37 formed in first tuft block 16. A second projection 34 also acts as a cam surface and engages an axial slot 35 formed in a second tuft block 38. Rotation of drive shaft 28 and transmission spindle 32 results in rotation of projections 34, 36. Because the eccentric portions of projections 34, 36 are mounted in slots 35, 37 of tuft blocks 16, 38, respectively, the rotational movement is transmitted to tuft blocks 16, 38 as an oscillating rotational movement to first tuft block 16, as shown by arrow 17 in FIG. 2, and as a side-to-side oscillating movement to second tuft block 38, as shown by arrows 46 in FIG. 2. Alternatively, tuft blocks 16, 38 could be driven by separate drive mechanisms having, for example, separate shafts. Such separate drive mechanisms are not preferred since it would require additional components and space requirements.

Second tuft block 38 may be a fixed section either having fixed bristles or bristles which can move independently of each other as a result of being mounted on an elastomeric base. Preferably, however, second tuft block 38 moves or oscillates. Second tuft block 38 preferably moves in and out in a direction generally perpendicular to the outer surface 26 of head 14, resulting in a vibrating section. The resulting in and out motion is indicated by arrow 42 in FIG. 3. Any suitable drive mechanism may be used to accomplish this in and out vibrating motion such as the type of drive member described in U.S. Pat. No. Re. 35,941, the disclosure of which being incorporated herein by reference in its entirety except where inconsistent with the express teachings of the present invention.

Figure 5:
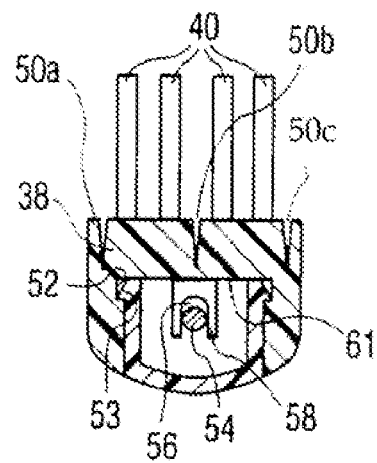
FIG. 5 is a cross-sectional view of the powered toothbrush head shown in FIGS. 1-4, taken along line 5-5 of FIG. 2 and showing the second tuft block and the second array of bristles extending therefrom in a first rest position.
Figure 6:
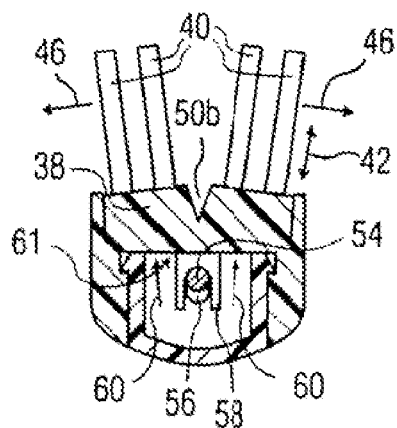
FIG. 6 is a cross-sectional view of the powered toothbrush head shown in FIGS. 1-5, taken along line 5-5 of FIG. 2 and showing the second tuft block and the second array of bristles extending therefrom in a second flexed position.

FIGS. 5 and 6 illustrate how a combination of in- and out motion 42 and side-to-side oscillating motion 46 may be accomplished with the second array of bristles 40 of the second tuft block 38 of the toothbrush 10 of the present invention. As shown, second tuft block 38 has a plurality of notches, such as 50a, 50b and 50c, formed therein, with notch 50b provided at a substantially central portion of second tuft block 38 having a relatively larger gap than the side notches 50a and 50c. Second tuft block 38 also includes recessed undercut portions 52 that receive and connect with beveled clip arms 53 of head 14. In one preferred embodiment, a drive mechanism includes a cam lobe 54 mounted onto an eccentric cam 56 provided on a transmission spindle (not shown, but similar or identical to spindle 32). Both cam lobe 54 and eccentric cam 56 are contained in a yolk 58 of a substantially inverted U-shape lying substantially adjacent to or abutting a lower central surface 61 of second tuft block 38. Preferably, as shown in FIGS. 5-6, yolk 58 lies substantially directly below the central notch 50 formed in second tuft block 38.

As eccentric cam 56 rotates from its first position shown in FIG. 5 to its second position shown in FIG. 6, cam lobe 54 forces yolk 58 and second tuft block 38 upwards, as shown by arrows 60. The force applied by cam lobe 54 flexes central notch 50b wider and flexes the other notches 50a and c (notches lying on either side of central notch 50) to a closed position. As further shown in FIG. 6, bristles 40 are also forced laterally outwardly, as shown by arrows 46 in FIG. 6.

Other forms of movement of second tuft block 38 could be as indicated by arrow 44 in FIG. 2 where the movement is parallel to the longitudinal axis of head 14. Preferably, however, second tuft block 38 moves perpendicular to the longitudinal axis of head 14, as indicated by arrows 46, and in-and-out as indicated by arrows 42, as described in detail above.

Thus, the present invention includes a first tuft block 16 mounted for rotational oscillation in a plane generally parallel to the outer surface of head 14, and a second tuft block 38 having fixed bristles or bristles independently movable by being mounted on an elastomeric base second tuft block 38 preferably moves laterally, transversely, or in and out. A third stationary tuft block 62 may optionally be provided below second tuft block 38 toward the neck portion 12 of the toothbrush 10. The bristles of tuft blocks 16, 38, 62 may be of any of the constructions previously described, may be of various lengths, colors and stiffness, and may be mounted perpendicularly to or at an angle to the outer surface of head 14. For instance, at least some of the bristles of any or all of the tuft blocks 16, 38, 62 can be natural bristles, that is, bristles made from animal hair.

It will be apparent to those skilled in the art that various modifications and variations can be made in the powered toothbrush of the present invention and in construction of the toothbrush without departing from the scope or spirit of the invention, examples of which have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A powered toothbrush having a handle with a neck portion extending from the handle, comprising:
   a head connected to said neck portion, said head having an exposed outer surface;
   a first tuft block mounted to said head, said first tuft block having a first array of bristles extending outwardly from the exposed outer surface of said head;
   a first drive member operatively connected to said first tuft block for rotating said first tuft block about a rotational axis that is generally perpendicular to the exposed outer surface of said head;
   a second tuft block mounted to said head closer to the neck portion than said first tuft block, said second tuft block having a second array of bristles extending outwardly from the exposed outer surface;
   a second drive member operatively connected to said second tuft block for moving said second tuft block in a direction generally perpendicular to the exposed outer surface of said head; and
   a third tuft block stationarily mounted to said head closer to said neck portion than either of said first and second tuft blocks, said third tuft block having a third array of bristles extending outwardly from the exposed outer surface of the head;
   a drive mechanism operably coupled to said first and second drive members; and
   wherein said drive mechanism comprises a motor and a drive shaft.

2. The powered toothbrush of claim 1, wherein said second tuft block oscillates in an in and out direction generally perpendicular to the exposed outer surface of the head.

3. The powered toothbrush of claim 1, wherein said first drive member and said second drive member are part of the same drive mechanism.

4. The powered toothbrush of claim 3, wherein said first, second and third arrays of bristles can be of various lengths.

5. The powered toothbrush of claim 3, wherein said first, second and third arrays of bristles can be of various colors.

6. The powered toothbrush of claim 3, wherein said first, second and third arrays of bristles can be of various stiffness.

7. A powered toothbrush having a handle with a neck portion extending from the handle, comprising:
   a head connected to said neck portion, said head having an exposed outer surface;
   a first tuft block mounted to said head, said first tuft block having a first array of bristles extending outwardly from the exposed outer surface of said head;
   a first drive member operatively connected to said first tuft block for rotating said first tuft block about a rotational axis that is generally perpendicular to the exposed outer surface of said head;
   a second tuft block mounted to said head closer to the neck portion than said first tuft block, said second tuft block having a second array of bristles extending outwardly from the exposed outer surface;
   a second drive member operatively connected to said second tuft block for moving said second tuft block in a direction generally perpendicular to the exposed outer surface of said head;
   a third tuft block stationarily mounted to said head closer to said neck portion than either of said first and second tuft blocks, said third tuft block having a third array of bristles extending outwardly from the exposed outer surface of the head; and
   a drive shaft with a longitudinal axis wherein said first and second drive members are portions of said drive shaft that are eccentric with respect to said longitudinal axis.

8. The powered toothbrush of claim 7, wherein said first drive member is a distal portion of said drive shaft and wherein said second drive member is an intermediate portion of said drive shaft positioned closer to said neck portion than said distal portion.

9. The powered toothbrush of claim 8, wherein said distal portion of said drive shaft is rotationally mounted in an axial slot in said first tuft block and wherein said intermediate portion of said drive shaft is rotationally mounted in an axial slot in said second tuft block.

* * * * *